United States Patent
Smith

(10) Patent No.: US 7,385,161 B2
(45) Date of Patent: *Jun. 10, 2008

(54) METHOD OF ESTIMATING THE TEMPERATURE OF AN OXYGEN SENSOR HEATING ELEMENT

(75) Inventor: James Craig Smith, Farmington Hills, MI (US)

(73) Assignee: Delphi Technologies, Inc., Troy, MI (US)

( * ) Notice: Subject to any disclaimer, the term of this patent is extended or adjusted under 35 U.S.C. 154(b) by 305 days.

This patent is subject to a terminal disclaimer.

(21) Appl. No.: 11/234,557

(22) Filed: Sep. 23, 2005

(65) Prior Publication Data
US 2007/0068917 A1    Mar. 29, 2007

(51) Int. Cl.
*H05B 1/02* (2006.01)
(52) U.S. Cl. .............. 219/494; 219/497; 219/505; 374/101; 374/185; 701/109; 73/25.01
(58) Field of Classification Search .......... 219/491, 219/494, 497, 499, 501, 505, 507, 508; 374/101, 374/120, 102, 185; 73/106, 23.2; 701/107, 701/105, 109, 25.01
See application file for complete search history.

(56) References Cited

U.S. PATENT DOCUMENTS

| | | | |
|---|---|---|---|
| 5,001,643 A | * | 3/1991 | Domino et al. ............. 701/109 |
| 6,336,354 B1 | * | 1/2002 | Suzuki et al. ............. 73/31.05 |
| 6,586,711 B2 | | 7/2003 | Whitney et al. |
| 6,742,379 B2 | * | 6/2004 | Matsubara et al. .......... 73/1.06 |

OTHER PUBLICATIONS

U.S. Appl. No. 10/835,188, filed Apr. 28, 2004, Smith.

* cited by examiner

*Primary Examiner*—Mark Paschall
(74) *Attorney, Agent, or Firm*—Paul L. Marshall

(57) ABSTRACT

The resistance of an oxygen sensor heating element is estimated by modeling the effects of physical and electrical heating on the resistance of the heating element lead-in conductors, and subtracting the lead-in conductor resistance from a measure of the heating circuit resistance. The lead-in conductor resistance model is based on the temperature of the oxygen sensor boss and the current carried by the lead-in conductors. The heating element temperature is calculated from the determined heating element resistance and initial (cold-start) parameters of the heating circuit.

9 Claims, 6 Drawing Sheets

METHOD OF ESTIMATING THE TEMPERATURE OF AN OXYGEN SENSOR HEATING ELEMENT

TECHNICAL FIELD

The present invention relates to heated exhaust-gas oxygen sensors, and more particularly to a method of estimating the temperature of the oxygen sensor heating element so that the temperature of the oxygen sensor may be accurately controlled.

BACKGROUND OF THE INVENTION

Exhaust-gas oxygen sensors are commonly equipped with an integral resistive heating element that is electrically activated following engine starting to quickly bring the oxygen sensor to a desired operating temperature. The control objective during the warm-up interval is to maintain the heating element at a target temperature such as 700° C. Since the actual temperature of the heating element cannot be conveniently measured, it is typically estimated based on a measurement of electrical resistance. However, heating element resistance varies not only with temperature, but also from sensor-to-sensor due to manufacturing tolerances. One way of addressing this problem is disclosed in the U.S. Pat. No. 6,586,711 to Whitney et al., where the resistance of the heating element is measured at a known starting temperature and a resistance offset is calculated based on the deviation of the measured resistance from a nominal value. Unfortunately, the resistance of the heating element cannot be directly measured with many oxygen sensors, and any resistance measurement will also include the resistance of the wiring harness and terminals, lead-in conductors, and so forth. While the resistance of the wiring harness and terminals may be neglected, many planar oxygen sensors include printed lead-in conductors whose resistance can be similar to that of the heating element. Accordingly, what is needed is a way of determining the resistance of the lead-in conductors to enable reliable estimation of the heater element resistance and temperature.

SUMMARY OF THE INVENTION

The present invention is directed to an improved method of estimating the temperature of an exhaust-gas oxygen sensor heating element, where the heating element is part of a heating circuit that additionally includes lead-in conductors, and where the electrical resistance of the lead-in conductors is estimated by modeling. The lead-in conductor resistance model is based on the temperature of the oxygen sensor boss and the current carried by the lead-in conductors. The modeled resistance of the lead-in conductors is subtracted from a measure of the heating circuit resistance to determine the resistance of the heating element, and the heating element temperature is calculated from the determined heating element resistance and initial (cold-start) parameters of the heating circuit.

BRIEF DESCRIPTION OF THE DRAWINGS

FIG. 6C graphically depicts a time constant variation for modeling changes in resistance $R_{LDS}$ due to electrical heating for various values of sensor boss temperature $T_{BOSS}$.

DESCRIPTION OF THE PREFERRED EMBODIMENT

Figure 1:
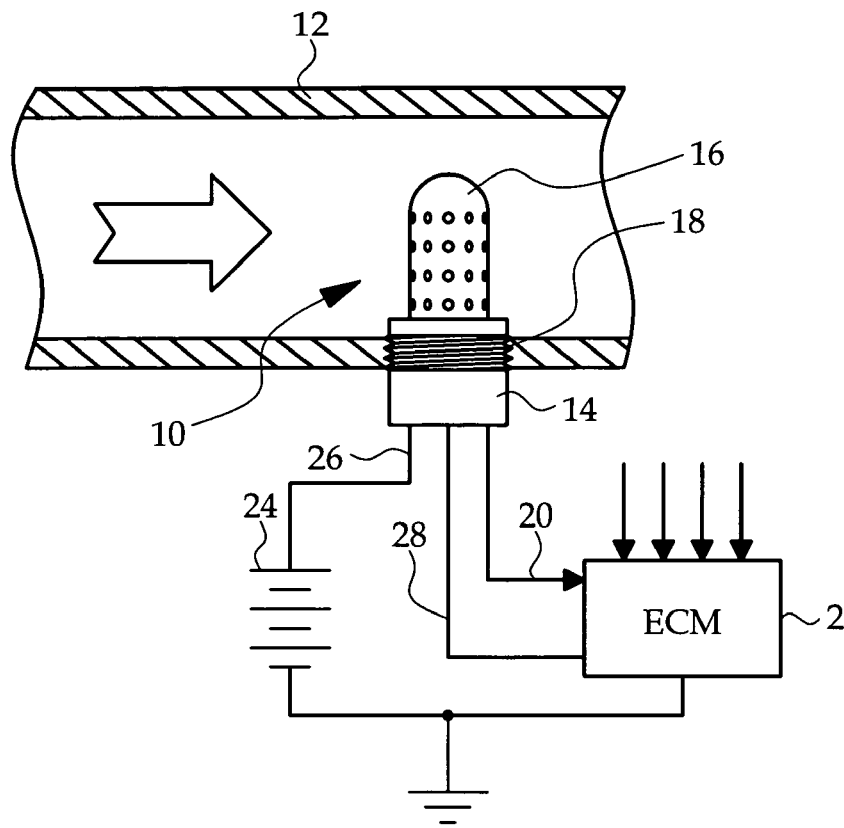
FIG. 1 is a diagram of a heated exhaust-gas oxygen sensor installed in an engine exhaust pipe and coupled to a microprocessor-based engine control module (ECM)

Referring to the drawings, and particularly to FIG. 1, the reference numeral 10 generally designates a heated exhaust-gas oxygen sensor installed on the exhaust header 12 of an internal combustion engine. The sensor 10 includes a mounting boss 14 and a perforated cover 16 surrounding a zirconia sensing element and a heating element. The mounting boss 14 is threaded into an opening 18 in the wall of exhaust header 12 so that the exhaust gases in the header 12 flow through the perforated cover 16 for detection by the zirconia sensing element. Preferably, the sensor 10 is a planar device such as the INTELLEK OSP sensor manufactured and sold by Delphi Corporation, in which the zirconia sensing element, the heating element and the heating element lead-in conductors are manufactured by depositing and firing specially formulated thick film inks on ceramic substrates. For a detailed description of the INTELLEK OSP sensor, see SAE Paper No. 2000-01-088, authored by Yoo, Bonadies, Detwiler, Ober and Reed, and presented in 2000. The oxygen sensor output signal on line 20 is supplied to a microprocessor-based engine control module (ECM) 22 for purposes of regulating the engine air-fuel ratio, and a vehicle storage battery 24 supplies power to the oxygen sensor heating circuit via line 26. The heating circuit is also coupled to line 28, and the ECM 22 controls heater activation by selectively connecting line 28 to the negative terminal of battery 24 (i.e., ground potential).

Figure 2:
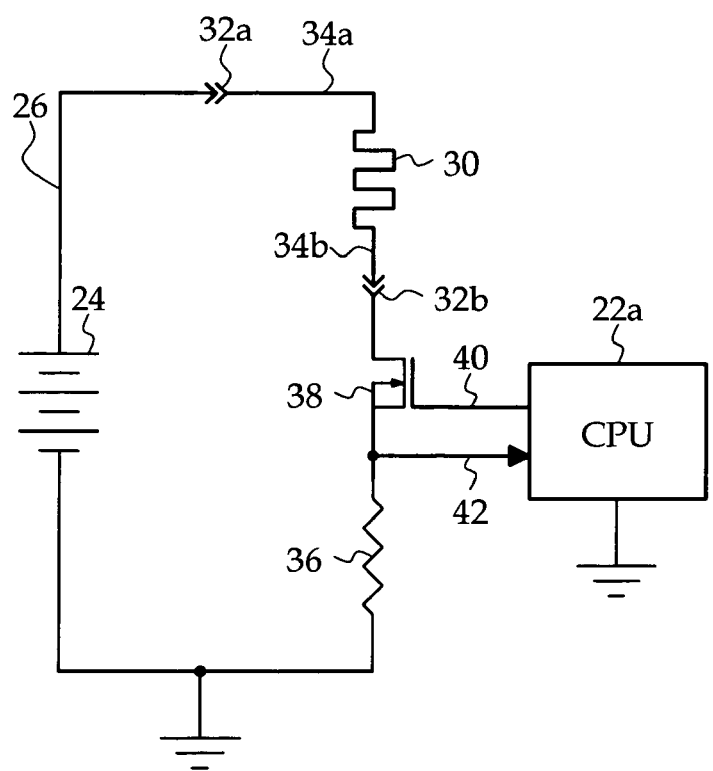
FIG. 2 is a circuit diagram of a heating circuit of the oxygen sensor of FIG. 1 including a serpentine resistor, and a control circuit for regulating electrical activation of the serpentine resistor.

Referring to FIG. 2, the heating element of oxygen sensor 10 is represented by the serpentine resistor 30, and the sensor heating circuit includes the resistor 30, connector terminal pairs 32a, 32b, and lead-in conductors 34a, 34b. The positive terminal of battery 24 is coupled to connector terminal pair 32a and the negative terminal of battery 24 is coupled to connector terminal pair 32b via sense resistor 36 and MOSFET 38. The sense resistor 36 and MOSFET 38 are preferably integrated into ECM 22. A central processing unit (CPU) 22a of ECM 22 modulates the conduction of MOSFET 38 via line 40 and samples the voltage across sense resistor 36 via line 42 as a measure of the current supplied to the heating circuit.

In operation, ECM 22 regulates the current supplied to the serpentine resistor 30 to quickly heat the zirconia sensing element of oxygen sensor 10 to a desired operating temperature such as 700° C., and to thereafter maintain it substantially at that temperature. While it can be reliably assumed that the temperatures of the sensing element and the serpentine resistor 30 are virtually the same due to close thermal coupling, that temperature must be estimated based on measured and known parameters, including the terminal voltage of battery 24, the supplied current, the thermal coefficient-of-resistance (TCR) of serpentine resistor 30, the on-resistance of MOSFET 38, the resistances of the connector terminal pairs 32a, 32b, lead-in conductors 34a, 34b, and serpentine resistor 30, and the resistance associated with the zirconia sensing element. In a conventional approach, the voltage, current and resistance parameters could be used to determine the overall resistance of the oxygen sensor heating circuit, with the TCR being used to convert the heating element resistance to a corresponding temperature. Unfortunately, estimation errors occur because manufacturing variations make it difficult to know how much of the determined resistance is due to the lead-in conductors 34a and 34b. These lead-in resistance variations produce a corresponding variation in the overall resistance of the heating circuit that is not related to the temperature of the serpentine resistor 30, thereby introducing error in the estimated temperature of the zirconia sensor element.

The method of the present invention overcomes the above-described difficulties by modeling the resistance of lead-in conductors 34a, 34b and subtracting the modeled resistance from a measure of the heating circuit resistance to determine resistance of the serpentine resistor 30. Once the resistance of serpentine resistor 30 is known, its temperature may be calculated based on its TCR and base resistance, and temperature calibration data.

Figure 3:
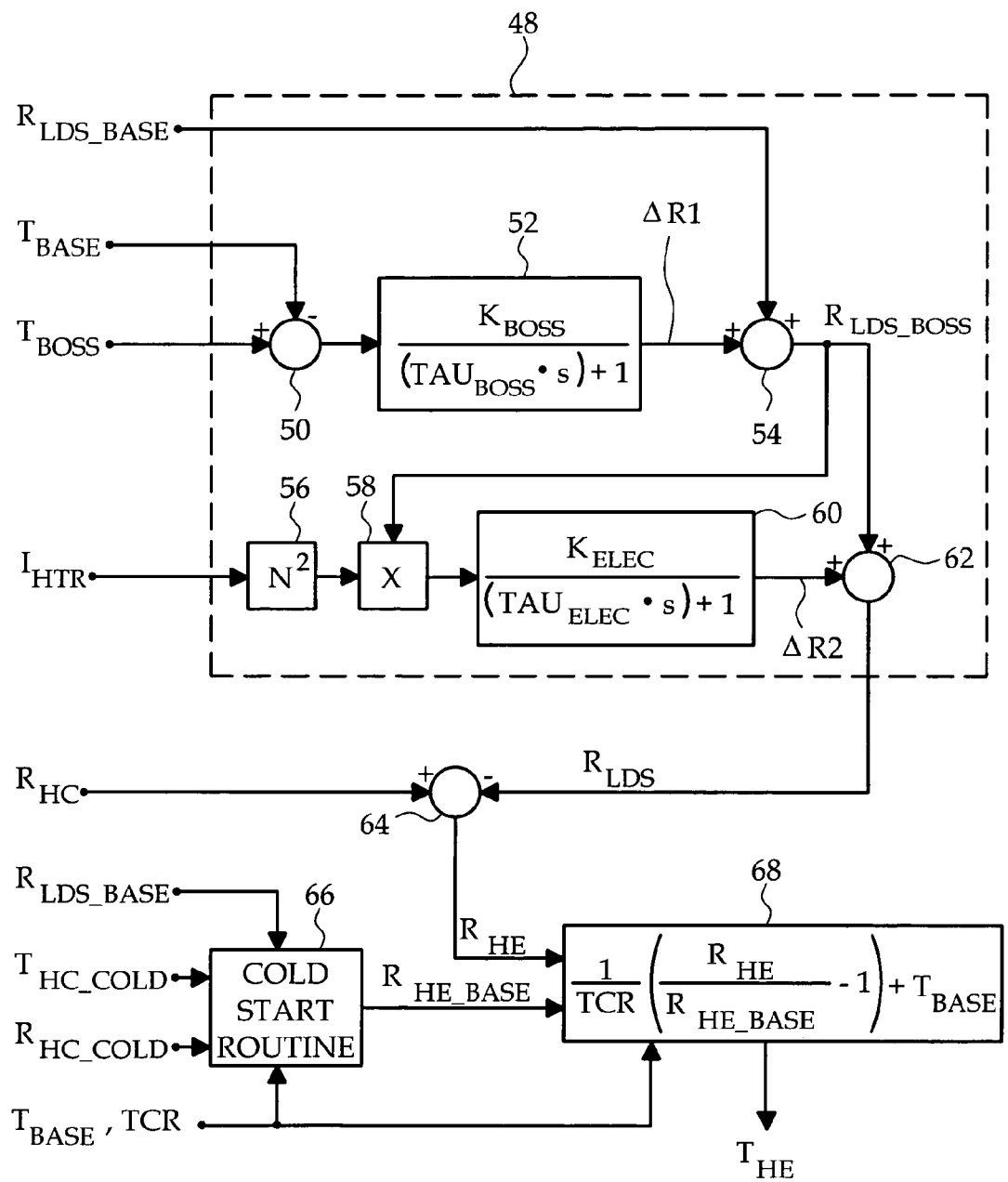
FIG. 3 is a block diagram of a heating element temperature estimation method carried out by the ECM of FIG. 1 according to this invention.

The block diagram of FIG. 3 depicts an estimation method carried out by ECM 22 according to this invention. The inputs include the measured heater circuit resistance $R_{HC}$, the cold-start heater circuit resistance $R_{HC\_COLD}$, the base lead-in conductor resistance $R_{LDS\_BASE}$, the base temperature $T_{BASE}$, the current $I_{HC}$ supplied to the heating circuit, and the temperature $T_{BOSS}$ of the oxygen sensor boss 14. The output is the heating element temperature $T_{HE}$—i.e., the temperature of serpentine resistor 30. A lead-in conductor resistance model 48 comprising the blocks 50-62 provides the lead-in conductor resistance $R_{LDS}$ as an intermediate output, and the blocks 64-68 utilize $R_{LDS}$ along with the serpentine resistor TCR, $R_{HC}$, $R_{HC\_COLD}$, and $R_{LDS\_BASE}$ to form the heating element temperature $T_{HE}$. The terms $R_{LDS\_BASE}$ and $T_{BASE}$ are calibration values as mentioned above; $R_{LDS\_BASE}$ is a known resistance of the lead-in conductors 34a, 34b at a base temperature $T_{BASE}$ such as 22° C. The term $R_{HC\_COLD}$ is a measure of the heater circuit resistance under cold-start conditions where the heater circuit temperature can be presumed to be the same as some other engine temperature such as the engine coolant temperature.

Figure 4:
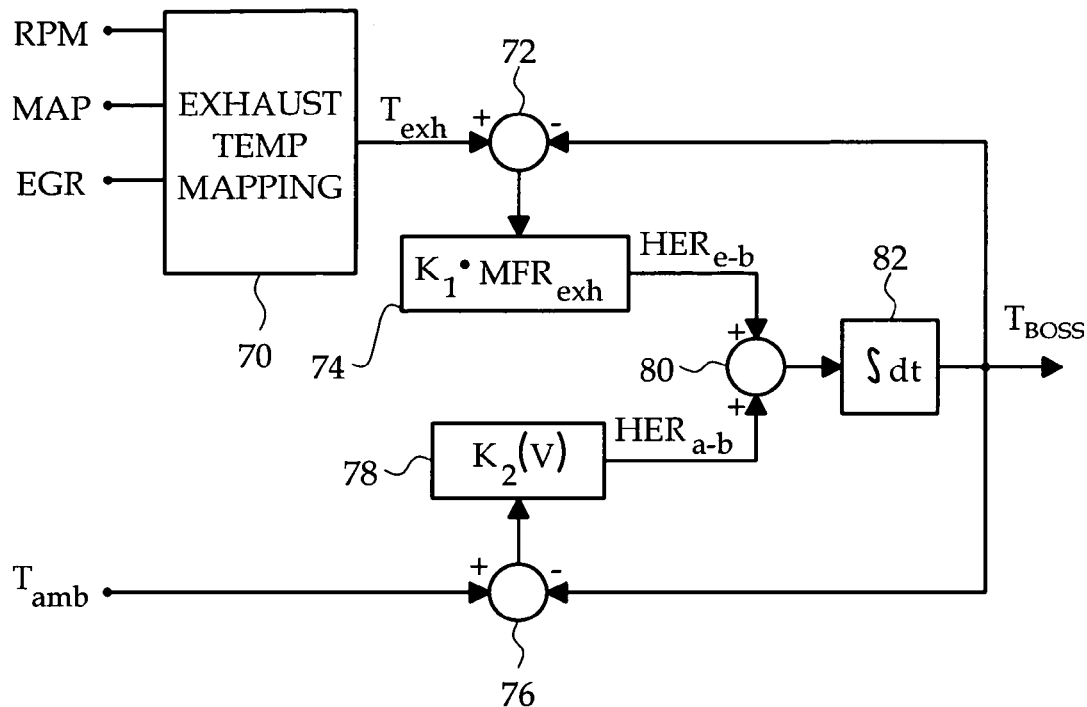
FIG. 4 is a block diagram of a model executed by the ECM of FIG. 1 for estimating the temperature $T_{BOSS}$ of an oxygen sensor boss according to a preferred embodiment of this invention.

The oxygen sensor boss temperature $T_{BOSS}$ may be measured if desired, but is preferably modeled based on engine operating parameters. FIG. 4 depicts a simplified version of such a model. Referring to FIG. 4, the block 70 designates a model or algorithm that maps the temperature $T_{exh}$ of exhaust gas in exhaust header 12 based on various engine operating parameters such as speed (RPM), intake manifold pressure (MAP) and exhaust gas recirculation percent (EGR). The temperature $T_{exh}$ and a feedback term $T_{BOSS}$ are differenced at block 72 and the difference is applied to the product (K1·MFR$_{exh}$) at block 74, where K1 is a gain constant and MFR$_{exh}$ is the mass flow rate of the exhaust gas. The result is the heat energy rate HER$_{e-b}$ between the exhaust gas and the oxygen sensor boss 14. Similarly, the $T_{amb}$ and the feedback term $T_{BOSS}$ are differenced at block 76 and the difference is applied to the product (K2·V) at block 78, where K2 is a gain constant and V is the mass flow rate of ambient air past the oxygen sensor boss 14. The result is the heat energy rate HER$_{a-b}$ between ambient air and the oxygen sensor boss 14. The two heat energy rates HER$_{e-b}$ and HER$_{a-b}$ are summed at block 80 and then integrated at block 82 to form the estimated sensor boss temperature $T_{BOSS}$.

Referring again to FIG. 3, the lead-in conductor resistance model 48 estimates $R_{LDS}$ as the sum of the base lead-in resistance $R_{LDS\_BASE}$, a first incremental lead-in resistance term ΔR1 provided by block 52 and a second incremental lead-in resistance term ΔR2 provided by block 60. The term ΔR1 is associated with conductive heat transfer to the lead-in conductors 34a, 34b from the sensor boss 14, and the term ΔR2 is associated with electrical heating of the lead-in conductors 34a, 34b due to the heating circuit current $I_{HC}$. In the illustrated embodiment, ΔR1 is modeled as a first-order function of the difference ($T_{BOSS}-T_{BASE}$) and ΔR2 is modeled as first-order function of the product $[(I_{HC})^2 \cdot R_{LDS\_BOSS}]$, where $R_{LDS\_BOSS}$ is the sum of $R_{LDS\_BASE}$ and ΔR1. The block 50 provides the difference input ($T_{BOSS}-T_{BASE}$) to block 52 and the blocks 56 and 58 provide the product input $[(I_{HC})^2 \cdot R_{LDS\_BOSS}]$ to block 60. The block 54 forms the sum ($R_{LDS\_BASE}+\Delta R1$) and the block 62 form the lead-in conductor resistance estimate $R_{LDS}$ according to the sum of $R_{LDS\_BOSS}$ and ΔR2.

The temperature $T_{HE}$ of serpentine resistor 30 is determined by subtracting the modeled lead-in conductor resistance $R_{LDS}$ from the measured heating circuit resistance $R_{HC}$ (block 64) to obtain the heating element resistance $R_{HE}$, and calculating $T_{HE}$ as a function of $R_{HE}$ and the base heating element resistance $R_{HE\_BASE}$ (block 68). The block 66 designates a routine executed under cold-start engine conditions for estimating the base heating element resistance $R_{HE\_BASE}$. Under cold-start conditions, the initial heating circuit temperature $T_{HC\_COLD}$ is set equal to a measure of engine coolant temperature or the like, and the cold-start resistance $R_{HC\_COLD}$ is measured by ECM 22. As indicated above, the resistance $R_{HC\_COLD}$ may be computed based on the battery voltage V_BATT (i.e., the driving voltage at the terminal pair 32a), the measured current $I_{HC}$, the heating circuit TCR, the on-resistance of MOSFET 38, the harness and connector resistances, and the resistance of sense resistor 36. Given $T_{HC\_COLD}$, $R_{HC\_COLD}$ and a nominal resistance $R_{LDS\_BASE}$ of the lead-in conductors 34a, 34b at the base temperature $T_{BASE}$, the block 66 calculates the cold-start lead-in conductor resistance $R_{LDS\_COLD}$ using the equation:

$$R_{LDS\_COLD}=R_{LDS\_BASE}[1+TCR \cdot (T_{HC\_COLD}-T_{BASE})]$$

where TCR is the thermal coefficient of resistance of the material used to form lead-in conductors 34a, 34b. The cold-start lead-in conductor resistance $R_{LDS\_COLD}$ is then subtracted from the measured cold-start heating circuit resistance $R_{HC\_COLD}$ to find the cold-start heating element resistance $R_{HE\_COLD}$. Given $T_{HC\_COLD}$, $R_{BASE}$ and $R_{HE\_COLD}$, the block 66 calculates the base heating element resistance $R_{HE\_BASE}$ (i.e., the resistance of serpentine resistor 30 at base temperature $T_{BASE}$) using the equation:

$$R_{HE\_BASE} = (M \cdot R_{HE\_COLD})/(T_{HC\_COLD} + M - T_{BASE})$$

where M is the reciprocal of TCR.

Figure 5A:
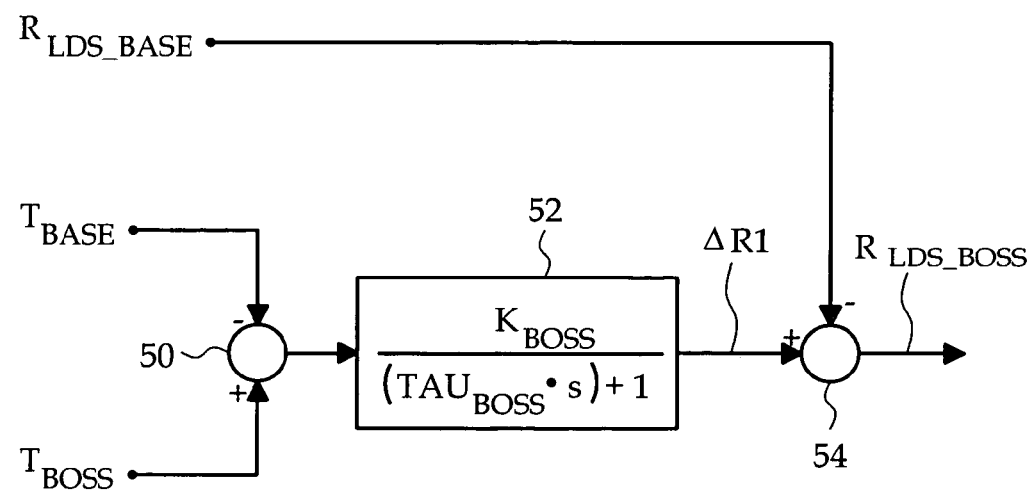
FIG. 5A is a block diagram of a portion of a model for estimating a resistance $R_{LDS}$ of internal lead-in conductors of the oxygen sensor of FIG. 1.
Figure 5B:
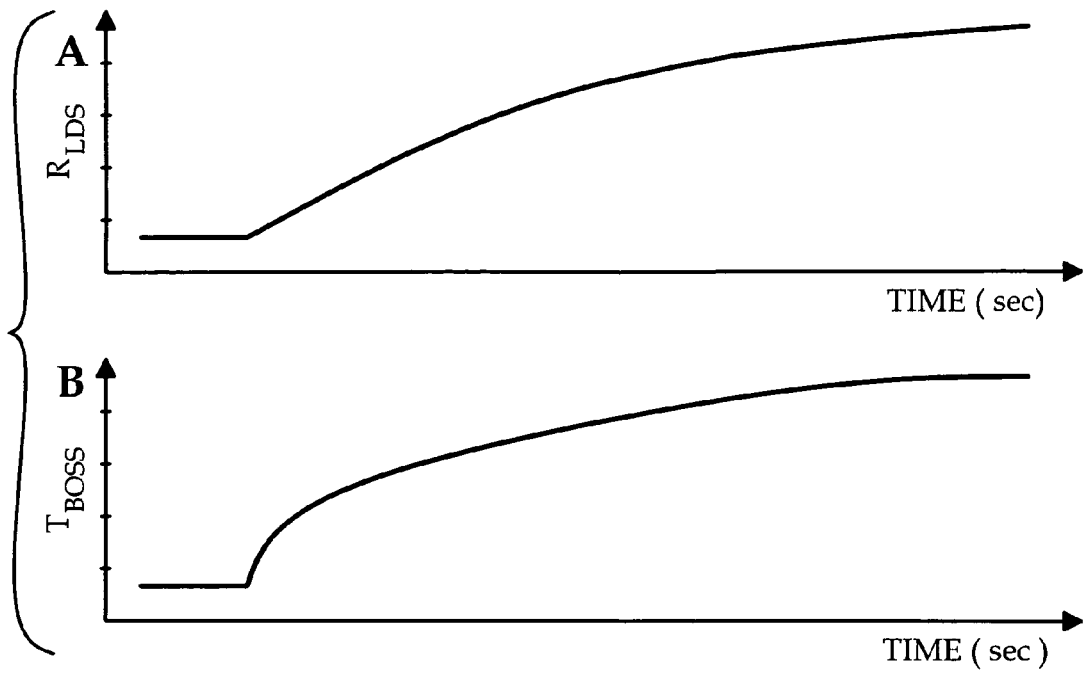
FIG. 5B, Graphs A and B, depict a measured variation in $R_{LDS}$ as the temperature $T_{BOSS}$ is increased over time while the sensor heating element is deactivated.
Figure 5C:
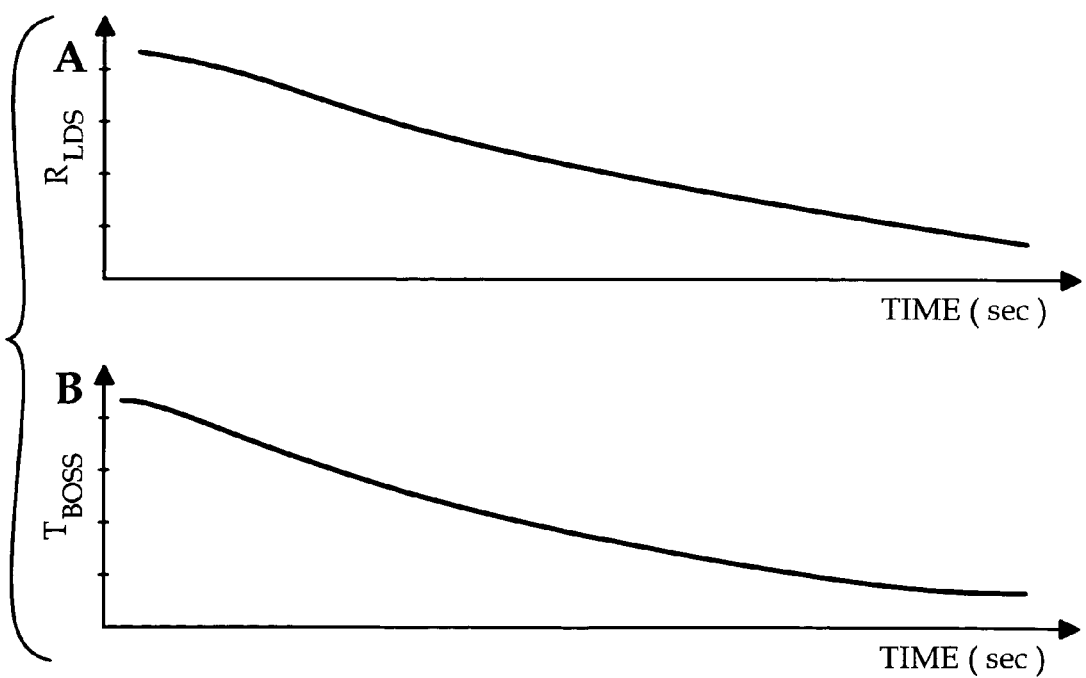
FIG. 5C, Graphs A and B, depict a measured variation in $R_{LDS}$ as the temperature $T_{BOSS}$ is decreased over time while the sensor heating element is deactivated.
Figure 6A:
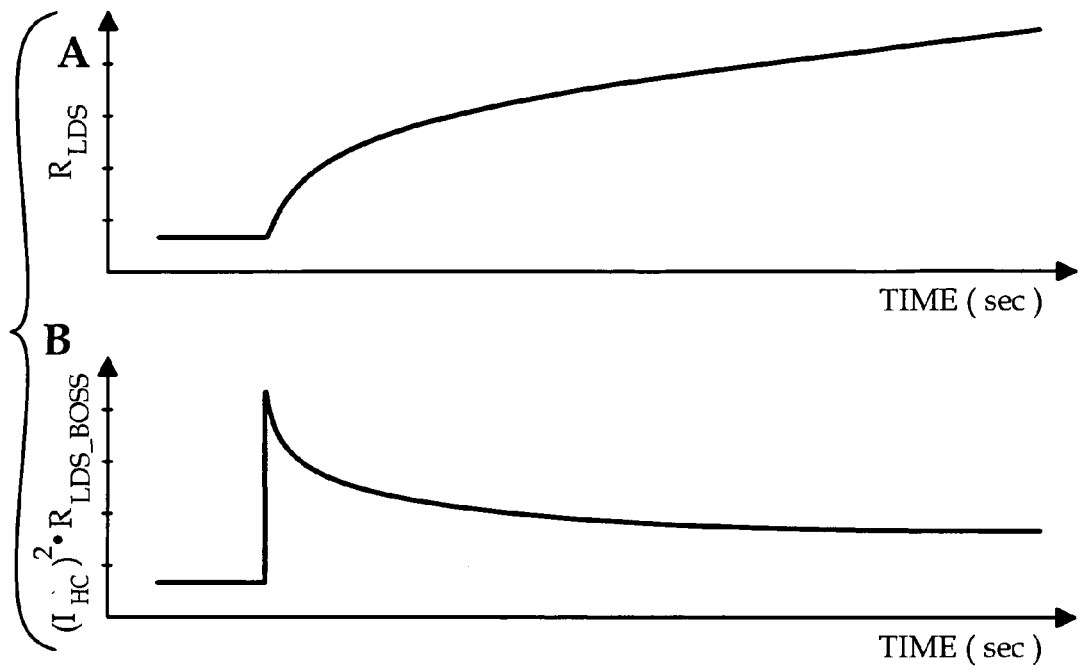
FIG. 6A, Graphs A and B, depict a measured variation in $R_{LDS}$ in response to a step increase in heating element activation duty cycle while the temperature $T_{BOSS}$ is maintained at a fixed value.
Figure 6B:
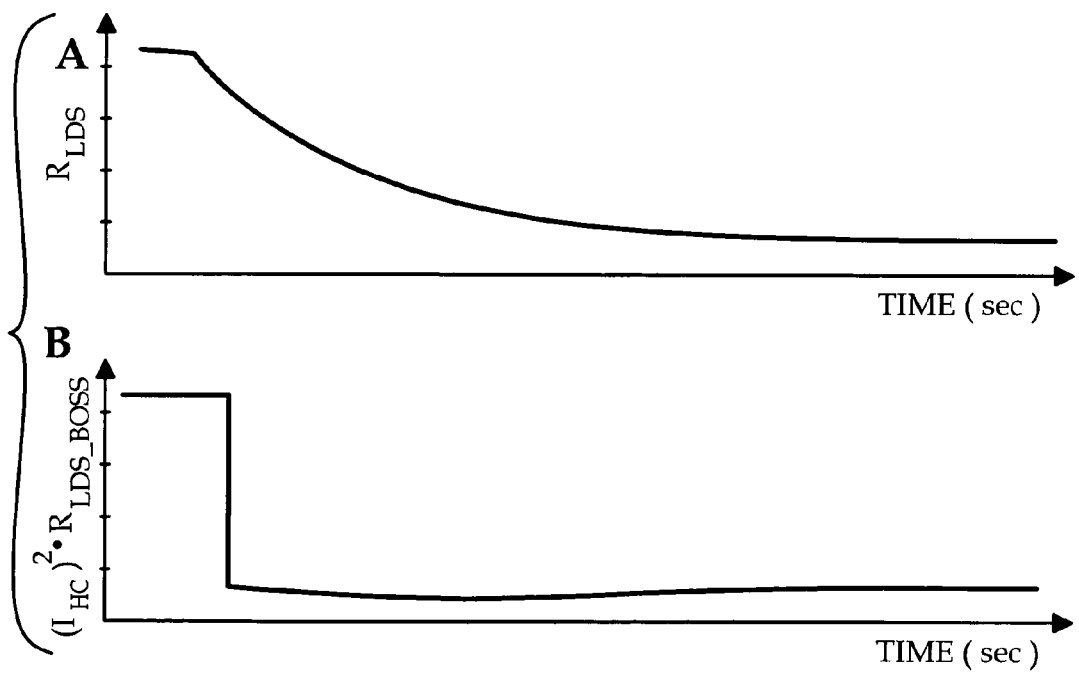
FIG. 6B, Graphs A and B, depict a measured variation in $R_{LDS}$ in response to a step decrease in heating element activation duty cycle while the temperature $T_{BOSS}$ is maintained at a fixed value.
Figure 6C:
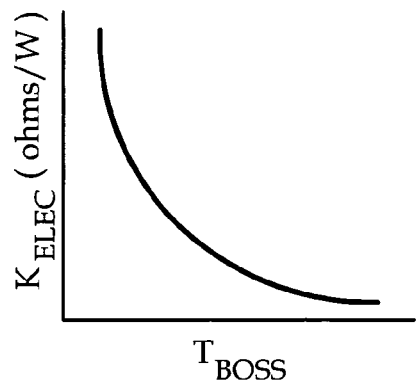
FIG. 6C graphically depicts a gain variation for modeling changes in resistance $R_{LDS}$ due to electrical heating for various values of sensor boss temperature $T_{BOSS}$.
Figure 6D:
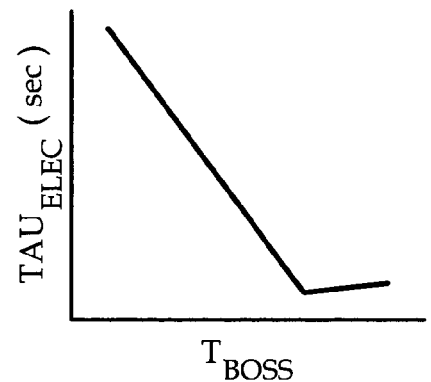

As indicated above, ΔR1 is modeled as a first-order function of the difference $(T_{BOSS} - T_{BASE})$ and ΔR2 is modeled as first-order function of product $[(I_{HC})^2 \cdot R_{LDS\_BOSS}]$. The respective gains $K_{BOSS}$, $K_{ELEC}$ and the respective time constants $TAU_{BOSS}$, $TAU_{ELEC}$ for a given vehicle configuration are determined by calibration. The calibration of $K_{BOSS}$ and $TAU_{BOSS}$ is described below in reference to FIGS. 5A-5C, and the calibration of $K_{ELEC}$ and $TAU_{ELEC}$ is described below in reference to FIGS. 6A-6D.

Gain $K_{BOSS}$ and time constant $TAU_{BOSS}$ for a given vehicle configuration are calibrated by forcing the temperature $T_{BOSS}$ of the oxygen sensor boss 14 to vary widely while maintaining MOSFET 38 non-conductive to rule out the effects of electrical heating. In this case, the output of summation block 54 represents the lead-in conductor resistance $R_{LDS}$ as shown in the abbreviated block diagram of FIG. 5A. The increase in $R_{LDS}$ due to increasing $T_{BOSS}$ is depicted in Graphs A-B of FIG. 5B, and the decrease in $R_{LDS}$ due to decreasing $T_{BOSS}$ is depicted in Graphs A-B of FIG. 5C. In each case, the data is used to characterize the $K_{BOSS}$ and $TAU_{BOSS}$. Although the gain $K_{BOSS}$ is the same for both increasing and decreasing values of $T_{BOSS}$, the time constant $TAU_{BOSS}$ is typically significantly higher for decreasing values of $T_{BOSS}$ than for increasing values of $T_{BOSS}$.

The electric heating related gain $K_{ELEC}$ and time constant $TAU_{ELEC}$ for a given vehicle configuration are calibrated by inducing step changes in the modulation duty cycle of MOSFET 38 while maintaining the oxygen sensor boss 14 at a fixed temperature. The increase in $R_{LDS}$ due to a step increase in the product $[(I_{HC})^2 \cdot R_{LDS\_BOSS}]$ for $T_{BOSS} = 30°$ C. is depicted in Graphs A-B of FIG. 6A, and the decrease in $R_{LDS}$ due to a step decrease in the product $[(I_{HC})^2 \cdot R_{LDS\_BOSS}]$ for $T_{BOSS} = 30°$ C. is depicted in Graphs A-B of FIG. 6B. The gain and time constant values $K_{ELEC}$ and $TAU_{ELEC}$ are determined and the process is then repeated for a different value of $T_{BOSS}$. Typically, both $K_{ELEC}$ and $TAU_{ELEC}$ will vary with $T_{BOSS}$, as graphically depicted in FIGS. 6C and 6D, respectively.

Figure 7:
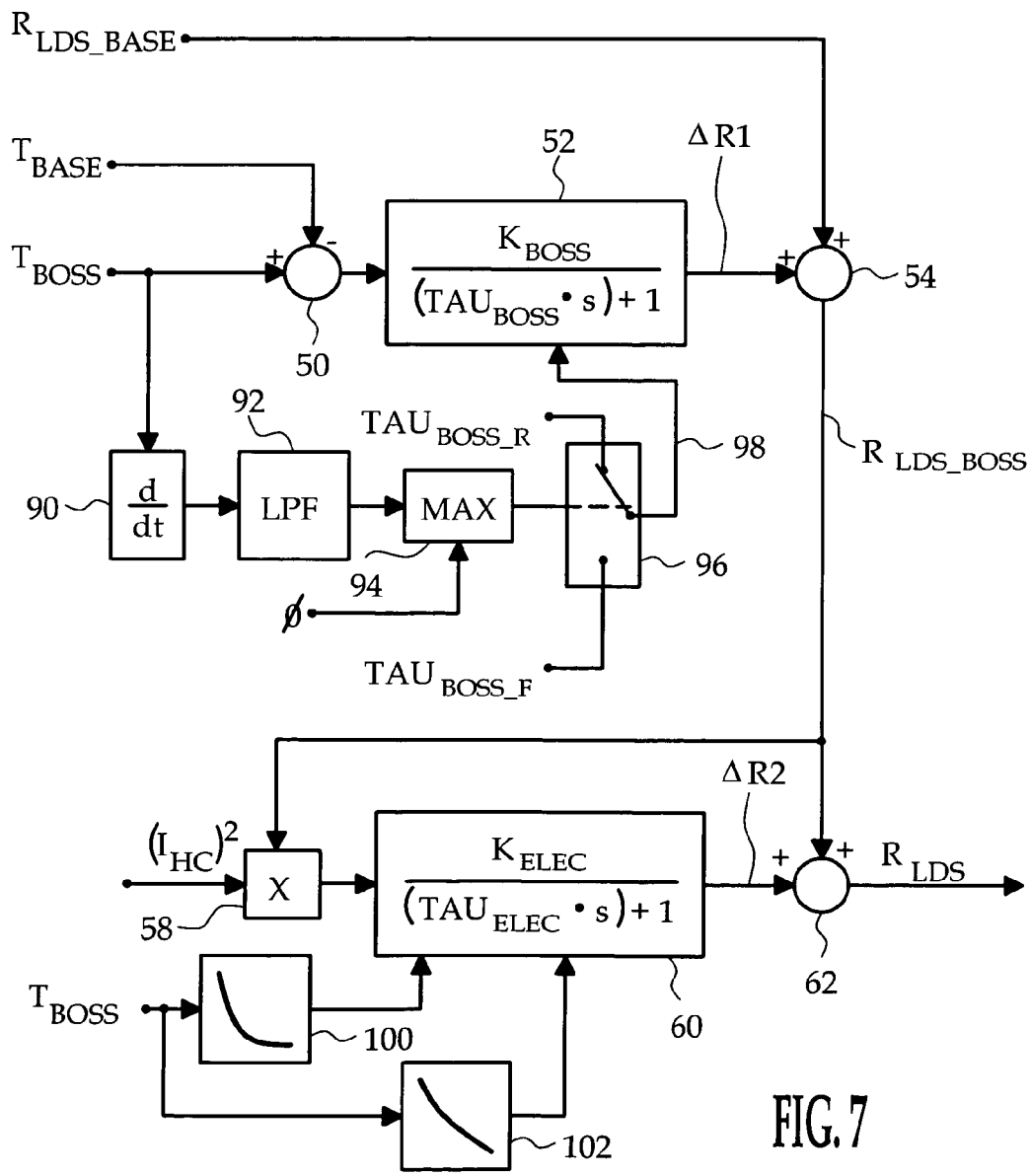
FIG. 7 is a block diagram of a mechanization of the $R_{LDS}$ resistance model according to this invention.

The block diagram of FIG. 7 represents an implementation of the lead-in conductor model 48, considering the aforementioned gain and time constant relationships. In respect to the first-order model of boss temperature effects (block 52), the blocks 90 and 92 differentiate and low-pass filter $T_{BOSS}$ to determine if $T_{BOSS}$ is increasing or decreasing, and max-value block 94 provides a digital representation of the result to switch block 96. If $T_{BOSS}$ is increasing, the switch block 96 assumes the depicted condition to supply block 52 the calibrated time constant $TAU_{BOSS\_R}$ for the case of rising boss temperature. Conversely, if $T_{BOSS}$ is decreasing, block 94 causes switch block 96 to supply block 52 the calibrated time constant $TAU_{BOSS\_F}$ for the case of falling boss temperature. In respect to the first-order model of electrical heating effects (block 60), the blocks 100 and 102 designate look-up tables characterizing the data depicted in FIGS. 6C and 6D. The block 100 provides block 60 with a calibrated value of $K_{ELEC}$ for the input $T_{BOSS}$, and the block 102 provides block 60 with a calibrated value of $TAU_{ELEC}$ for the input $T_{BOSS}$.

In summary, the method of the present invention provides a way of determining the resistance of lead-in conductors 34a, 34b to enable reliable estimation of the resistance and temperature of serpentine resistor 30. The lead-in conductor resistance model 48 is easily implemented in real time in a conventional ECM 22 and enables optimal performance of the oxygen sensor 10. The model 48 is empirical in nature and is superior to more complex physically-based models because it is concise in structure and simple to calibrate. While the present invention has been described with respect to the illustrated embodiment, it is recognized that numerous modifications and variations in addition to those mentioned herein will occur to those skilled in the art. For example, the incremental lead-in conductor resistances $R_{LDS\_BOSS}$ and $R_{LDS\_E}$ may be modeled as second or higher order functions of the respective inputs, and so on. Accordingly, it is intended that the invention not be limited to the disclosed embodiment, but that it have the full scope permitted by the language of the following claims.

The invention claimed is:

1. A temperature estimation method for a heating element of an exhaust-gas oxygen sensor having an installation boss and an internal heating circuit including said heating element and a set of lead-in conductors, the method comprising the steps of:
   determining a temperature of the sensor boss;
   measuring an electrical current supplied to said heating circuit and an electrical resistance of said heating circuit;
   modeling an electrical resistance of said lead-in conductors based on the determined boss temperature and the measured electrical current;
   calculating an electrical resistance of said heating element based on the measured electrical resistance of said heating circuit and the modeled electrical resistance of said lead-in conductors; and
   estimating a temperature of said heating element based on its calculated electrical resistance and measured cold-start parameters of said heating circuit.

2. The temperature estimation method of claim 1, where the step of modeling an electrical resistance of said lead-in conductors includes the steps of:
   calibrating a base resistance value of said lead-in conductors;
   modeling a first incremental lead-in conductor resistance due to heating of said lead-in conductors by said sensor boss;
   modeling a second incremental lead-in conductor resistance due to heating of said lead-in conductors by said electrical current; and
   modeling the electrical resistance of said lead-in conductors according to a sum of said base resistance value, said first incremental lead-in conductor resistance and said second incremental lead-in conductor resistance.

3. The temperature estimation method of claim 2, wherein:
   said base resistance value is calibrated at a base temperature; and
   the first incremental lead-in conductor resistance is modeled as a function of a difference between said base temperature and the determined temperature of said sensor boss.

4. The temperature estimation method of claim 3, including the steps of:

modeling said first incremental lead-in conductor resistance as a first order function of the difference between said base temperature and the determined temperature of said sensor boss; and calibrating a gain and time constant of said first order function by measuring the resistance of said lead-in conductors while varying the temperature of said sensor boss, with no electrical current supplied to said heating circuit.

5. The temperature estimation method of claim 3, including the steps of:

determining a direction of change in the determined temperature of said sensor boss; and selecting a calibrated time constant for modeling said first incremental lead-in conductor resistance based on the determined direction of change.

6. The temperature estimation method of claim 2, wherein:

the second incremental lead-in conductor resistance is modeled as a function of said measured electrical current and a sum of said base resistance value and said first incremental lead-in conductor resistance.

7. The temperature estimation method of claim 6, including the steps of:

modeling said second incremental lead-in conductor resistance as a first order function of said measured electrical current and the sum of said base resistance value and said first incremental lead-in conductor resistance; and calibrating a gain and time constant of said first order function by measuring the resistance of said lead-in conductors while varying the electrical current supplied to said heating circuit, with no variation in the temperature of said sensor boss.

8. The temperature estimation method of claim 7, including the step of:

changing the temperature of said sensor boss and repeating the step of measuring the resistance of said lead-in conductors while varying the electrical current supplied to said heating circuit.

9. The temperature estimation method of claim 8, including the steps of:

storing said calibrated gain and time constant for different temperatures of said sensor boss; and retrieving a stored gain and a stored time constant for modeling said second incremental lead-in conductor resistance based on the determined temperature of said sensor boss.

* * * * *